US012794015B2

(12) United States Patent
Yang et al.

(10) Patent No.: US 12,794,015 B2
(45) Date of Patent: Nov. 10, 2026

(54) ADDITIVE FOR ELECTROLYTE, ELECTROLYTE FOR RECHARGEABLE LITHIUM BATTERY, AND RECHARGEABLE LITHIUM BATTERY INCLUDING THE SAME

(71) Applicant: SAMSUNG SDI CO., LTD., Yongin-si (KR)

(72) Inventors: Yeji Yang, Yongin-si (KR); Sangwoo Park, Yongin-si (KR); Sundae Kim, Yongin-si (KR); Sanghoon Kim, Yongin-si (KR); Hyunbong Choi, Yongin-si (KR); Hongryeol Park, Yongin-si (KR); Dahyun Kim, Yongin-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 559 days.

(21) Appl. No.: 18/464,904

(22) Filed: Sep. 11, 2023

(65) Prior Publication Data

US 2024/0222704 A1 Jul. 4, 2024

(30) Foreign Application Priority Data

Dec. 20, 2022 (KR) ........................ 10-2022-0179660

(51) Int. Cl.
*H01M 10/0567* (2010.01)
*C07D 213/80* (2006.01)
(Continued)

(52) U.S. Cl.
CPC ...... *H01M 10/0567* (2013.01); *C07D 213/80* (2013.01); *C07D 239/28* (2013.01);
(Continued)

(58) Field of Classification Search
CPC ............ H01M 10/0567; H01M 4/366; H01M 4/386; H01M 4/505; H01M 4/525;
(Continued)

(56) References Cited

U.S. PATENT DOCUMENTS 9,548,490 B2 1/2017 Ku et al.
10,923,768 B2 2/2021 Yu et al.
(Continued)

FOREIGN PATENT DOCUMENTS

KR 10-2103898 B1 4/2020
KR 10-2020-0074902 A 6/2020
(Continued)

OTHER PUBLICATIONS

International Search Report, mailed Sep. 8, 2023, corresponding to PCT/KR2023/002892, 4 pages.
Written Opinion of the International Search Authority, mailed Sep. 8, 2023, corresponding to PCT/KR2023/002892, 5 pages.
Office Action dated Jan. 7, 2026 issued in corresponding Korean Patent Application No. 10-2022-0179660, 12 pages.

*Primary Examiner* — James M Erwin
(74) *Attorney, Agent, or Firm* — Womble Bond Dickinson (US) LLP

(57) ABSTRACT

An additive for an electrolyte represented by Chemical Formula 1, and an electrolyte for a rechargeable lithium battery and a rechargeable lithium battery including the same are provided. The details of Chemical Formula 1 are as described in the specification.

21 Claims, 2 Drawing Sheets

(51) Int. Cl.

| | |
|---|---|
| ***C07D 239/28*** | (2006.01) |
| ***H01M 4/36*** | (2006.01) |
| ***H01M 4/38*** | (2006.01) |
| ***H01M 4/505*** | (2010.01) |
| ***H01M 4/525*** | (2010.01) |
| ***H01M 4/583*** | (2010.01) |
| ***H01M 10/0525*** | (2010.01) |
| ***H01M 10/0569*** | (2010.01) |
| ***H01M 10/44*** | (2006.01) |
| *H01M 4/02* | (2006.01) |

(52) U.S. Cl.
CPC ........... *H01M 4/366* (2013.01); *H01M 4/386* (2013.01); *H01M 4/505* (2013.01); *H01M 4/525* (2013.01); *H01M 4/583* (2013.01); *H01M 10/0525* (2013.01); *H01M 10/0569* (2013.01); *H01M 10/44* (2013.01); *H01M 2004/027* (2013.01); *H01M 2004/028* (2013.01); *H01M 2300/0037* (2013.01); *H01M 2300/0051* (2013.01)

(58) Field of Classification Search
CPC ............. H01M 4/583; H01M 10/0525; H01M 10/0569; H01M 10/44; H01M 2004/027; H01M 2004/028; H01M 2300/0037; H01M 2300/0051; C07D 213/80; C07D 239/28
USPC .......................................................... 429/326
See application file for complete search history.

(56) References Cited

U.S. PATENT DOCUMENTS

| | | | | |
|---|---|---|---|---|
| 2015/0243969 | A1 | 8/2015 | Ku et al. | |
| 2019/0334207 | A1 | 10/2019 | Yu et al. | |
| 2020/0044287 | A1 | 2/2020 | Kim et al. | |
| 2020/0251777 | A1 | 8/2020 | Lim et al. | |
| 2021/0226203 | A1 * | 7/2021 | Liu ...................... | H01M 4/525 |
| 2021/0328266 | A1 | 10/2021 | Kim et al. | |
| 2022/0115701 | A1 | 4/2022 | An et al. | |
| 2022/0140391 | A1 | 5/2022 | Kim et al. | |
| 2022/0223911 | A1 | 7/2022 | Kim et al. | |
| 2022/0315435 | A1 * | 10/2022 | Mizuno ................ | H01M 4/131 |
| 2022/0329841 | A1 | 10/2022 | Zheng | |
| 2022/0393166 | A1 | 12/2022 | Qiao et al. | |
| 2023/0039461 | A1 | 2/2023 | Gou et al. | |
| 2023/0053967 | A1 | 2/2023 | Zhang et al. | |
| 2023/0327203 | A1 | 10/2023 | Kim et al. | |

FOREIGN PATENT DOCUMENTS

| | | | |
|---|---|---|---|
| KR | 10-2020-0092889 | A | 8/2020 |
| KR | 10-2020-0105227 | A | 9/2020 |
| KR | 10-2167592 | B1 | 10/2020 |
| KR | 10-2192087 | B1 | 12/2020 |
| KR | 10-2021-0023756 | A | 3/2021 |
| KR | 10-2270869 | B1 | 7/2021 |
| KR | 10-2021-0138937 | A | 11/2021 |
| KR | 10-2022-0061723 | A | 5/2022 |
| KR | 10-2022-0104785 | A | 7/2022 |

* cited by examiner

ADDITIVE FOR ELECTROLYTE, ELECTROLYTE FOR RECHARGEABLE LITHIUM BATTERY, AND RECHARGEABLE LITHIUM BATTERY INCLUDING THE SAME

CROSS-REFERENCE TO RELATED APPLICATION

This application claims priority to and the benefit of Korean Patent Application No. 10-2022-0179660, filed in the Korean Intellectual Property Office on Dec. 20, 2022, the entire content of which is incorporated herein by reference.

BACKGROUND

1. Field

According to embodiments, the present disclosure relates to an additive for an electrolyte, and an electrolyte for a rechargeable lithium battery, and a rechargeable lithium battery including the same.

2. Description of the Related Art

A rechargeable lithium battery may be recharged and has three or more times as high energy density per unit weight as a comparable lead storage battery, nickel-cadmium battery, nickel hydrogen battery, nickel zinc battery and/or the like. It may be also charged at a high rate and thus, is commercially manufactured for a laptop, a cell phone, an electric tool, an electric bike, and/or the like, and researches on improvement of additional energy density have been actively made.

Such a rechargeable lithium battery is manufactured by injecting an electrolyte into a battery cell, which includes a positive electrode including a positive electrode active material capable of intercalating/deintercalating lithium ions and a negative electrode including a negative electrode active material capable of intercalating/deintercalating lithium ions.

The electrolyte serves as a medium for moving lithium ions between the negative electrode and the positive electrode, and in general, an organic solvent in which a lithium salt is dissolved is utilized, and this electrolyte is important in determining the stability and performance of a rechargeable lithium battery.

The electrolyte may include, for example, a mixed solvent of a high dielectric cyclic carbonate such as propylene carbonate and ethylene carbonate and a chain carbonate such as diethyl carbonate, ethylmethyl carbonate, dimethyl carbonate to which a lithium salt of $LiPF_6$, $LiBF_4$, LiFSI, and/or the like is added. As the development of batteries in one or more suitable fields is activated, the development of batteries with high output and high stability in a wide temperature range is becoming more important. In terms of electrolyte, it is important to develop an optimal or suitable combination of an organic solvent and an additive capable of improving high output, long cycle-life, high-temperature storage, and suppressing swelling, capacity reduction, and resistance increase.

SUMMARY

According to embodiments, an additive for an electrolyte has excellent or suitable high-temperature characteristics.

According to embodiments, an electrolyte for a rechargeable lithium battery includes the additive.

According to embodiments, a rechargeable lithium battery includes the electrolyte.

According to embodiments, an additive for an electrolyte is represented by Chemical Formula 1.

Chemical Formula 1

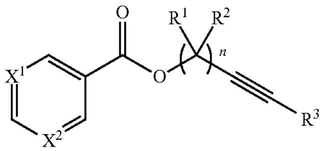

In Chemical Formula 1, $X^1$ and $X^2$ may each independently be N or $CR^a$, at least one of $X^1$ and $X^2$ is N, $R^a$ and $R^1$ to $R^3$ may each independently be hydrogen or a substituted or unsubstituted C1 to C10 alkyl group, and n is one of integers of 1 to 3.

The n may be an integer of 1 or 2.

$R^1$ to $R^3$ may each independently be hydrogen or a substituted or unsubstituted C1 to C5 alkyl group.

$R^3$ may be hydrogen.

The additive for an electrolyte may be one selected from among compounds listed in Group 1.

Group 1

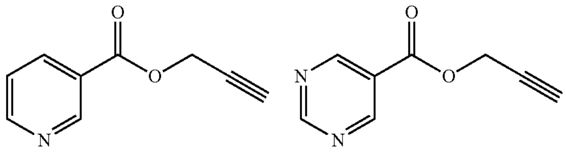

Another embodiment of the present disclosure provides an electrolyte for a rechargeable lithium battery including a non-aqueous organic solvent, a lithium salt, and the additive for the electrolyte.

The additive for the electrolyte may be included in an amount of about 0.05 to 5.0 parts by weight based on 100 parts by weight of the electrolyte for the rechargeable lithium battery.

The additive for the electrolyte may be included in an amount of about 0.05 to 3.0 parts by weight based on 100 parts by weight of the electrolyte for the rechargeable lithium battery.

The electrolyte for the rechargeable lithium battery may further include at least one other additive selected from among vinylene carbonate (VC), fluoroethylene carbonate (FEC), difluoroethylene carbonate, chloroethylene carbonate, dichloroethylene carbonate, bromoethylene carbonate, dibromoethylene carbonate, nitroethylene carbonate, cyanoethylene carbonate, vinylethylene carbonate (VEC), adiponitrile (AN), succinonitrile (SN), 1,3,6-hexane tricyanide (HTCN), propenesultone (PST), propanesultone (PS), lithium tetrafluoroborate ($LiBF_4$), lithium difluorophosphate ($LiPO_2F_2$), and 2-fluoro biphenyl (2-FBP).

The non-aqueous organic solvent may be composed of only chain carbonate.

The chain carbonate may be represented by Chemical Formula 2.

Chemical Formula 2

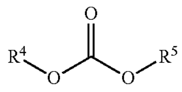

In Chemical Formula 2

$R^4$ and $R^5$ may each independently be a substituted or unsubstituted C1 to C20 alkyl group.

The non-aqueous organic solvent may be at least two selected from among dimethyl carbonate (DMC), diethyl carbonate (DEC), dipropyl carbonate (DPC), methylpropyl carbonate (MPC), ethylpropyl carbonate (EPC), and ethylmethyl carbonate (EMC).

Another embodiment of the present disclosure provides a rechargeable lithium battery including a positive electrode including a positive electrode active material; a negative electrode including a negative electrode active material; and the aforementioned electrolyte for the rechargeable lithium battery.

The positive electrode active material may include cobalt-free lithium nickel manganese oxide.

The cobalt-free lithium nickel manganese oxide may include lithium composite oxide represented by Chemical Formula 4.

Chemical Formula 4

$$Li_aNi_xMn_yM1_zM2_wO_{2\pm b}X_c$$

In Chemical Formula 4, $0.9 \le a < 1.2$, $0 \le b < 0.1$, $0 \le c < 0.1$, $0 \le w < 0.1$, $0.6 \le x < 1.0$, $0 < y < 0.4$, $0 < z < 0.1$, $w+x+y+z=1$, M1 and M2 may each independently be at least one element selected from among Al, Mg, Ti, Zr, Cr, Sr, V, B, W, Mo, Nb, Si, Ba, Ca, Ce, Cr, Fe, and Nb, and X is at least one element selected from among S, F, P, and Cl.

Chemical Formula 4 may be represented by Chemical Formula 4-1.

Chemical Formula 4-1

$$Li_aNi_{x1}Mn_{y1}Al_{z1}M2_{w1}O_{2\pm b}X_c$$

In Chemical Formula 4-1, $0.9 \le a < 1.2$, $0 \le b < 0.1$, $0 \le c < 0.1$, $0 \le w1 < 0.1$, $0.6 \le x1 < 1.0$, $0 < y1 < 0.4$, $0 < z1 < 0.1$, $w1+x1+y1+z1=1$, M2 is an element selected from among Mg, Ti, Zr, Cr, Sr, V, B, W, Mo, Nb, Si, Ba, Ca, Ce, Cr, Fe, and Nb, and X is at least one element selected from among S, F, P, and Cl.

In Chemical Formula 4-1, x1 may be $0.6 \le x1 \le 0.79$, y1 may be $0.2 \le y1 \le 0.39$, and z1 may be $0.01 \le z1 < 0.1$.

The negative electrode active material may include at least one of graphite and Si composite.

The Si composite may include a core including Si-based particles and an amorphous carbon coating layer.

The Si-based particles may include at least one of Si particles, a Si—C composite, $SiO_x$ ($0 < x \le 2$), and a Si alloy.

According to embodiments, the rechargeable lithium battery is capable of suppressing an increase in battery resistance during high-temperature storage and implementing excellent or suitable cycle life characteristics

1 BRIEF DESCRIPTION OF THE DRAWINGS

The above and/or other embodiments will become apparent and more readily appreciated from the following description of the embodiments, taken in conjunction with the accompanying drawings in which.

DETAILED DESCRIPTION

Figure 1:
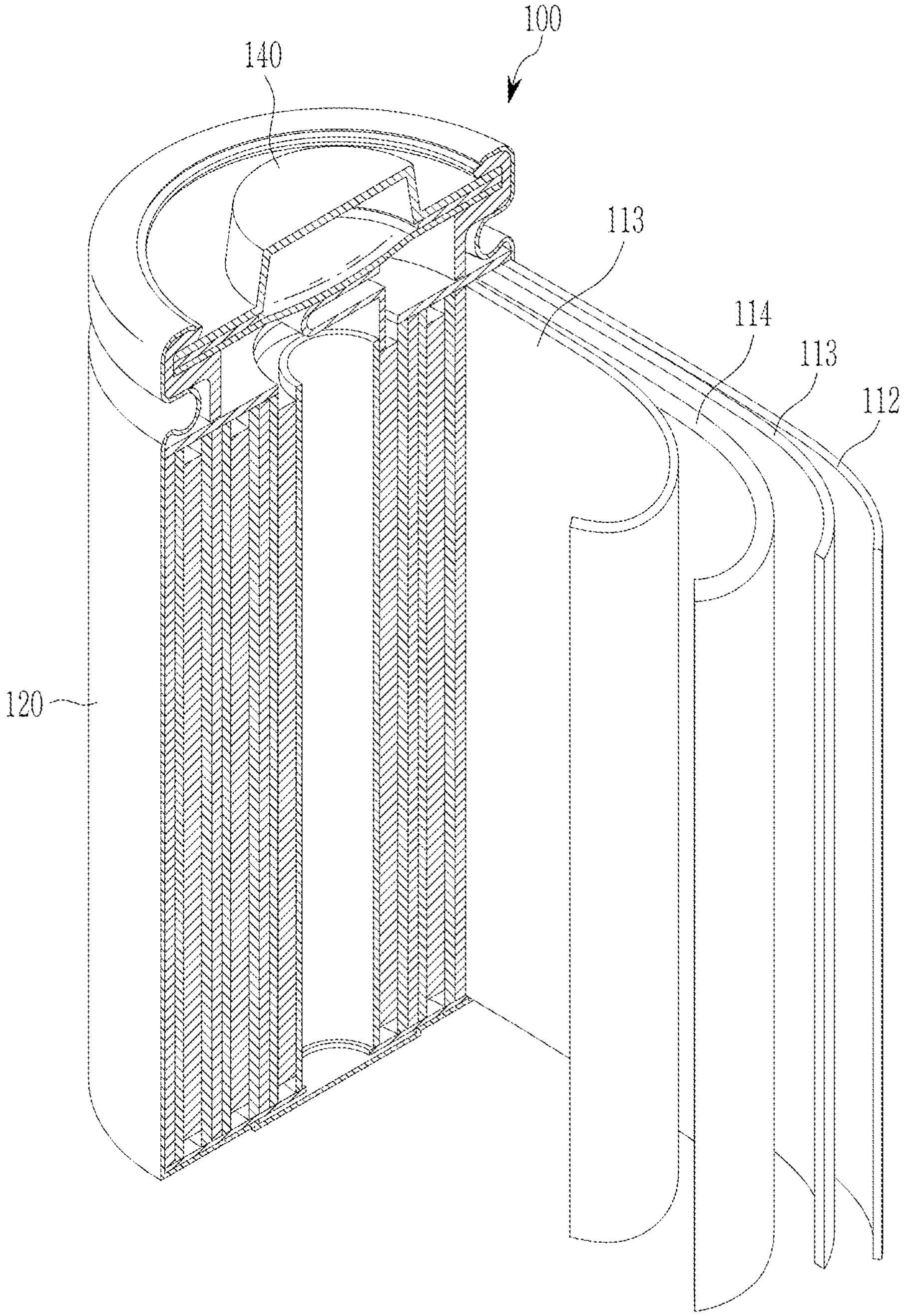
FIG. 1 is a schematic view of a rechargeable lithium battery according to one or more embodiments of the present disclosure.

Hereinafter, a rechargeable lithium battery according to one or more embodiments of the present disclosure will be described in more detail with reference to the accompanying drawings. However, these embodiments are example, the present disclosure is not limited thereto and the present disclosure is defined by the scope of claims. The present disclosure may be modified in many alternate forms, and is intended to cover all modifications, equivalents, and alternatives falling within the spirit and scope of the present disclosure.

The terminology utilized herein describes embodiments only, and is not intended to limit the present disclosure. The singular expression includes the plural expression unless the context clearly dictates otherwise. Unless otherwise defined, all chemical names, technical and scientific terms, and terms defined in common dictionaries should be interpreted as having meanings consistent with the context of the related art, and should not be interpreted in an ideal or overly formal sense. It will be understood that, although the terms first, second, etc. may be used herein to describe various elements, these elements should not be limited by these terms. These terms are only used to distinguish one element from another element. Thus, a first element could be termed a second element without departing from the teachings of the present disclosure. Similarly, a second element could be termed a first element.

As utilized herein, "combination thereof" refers to a mixture, laminate, composite, copolymer, alloy, blend, reaction product, and/or the like of the constituents.

As utilized herein, terms such as "comprises," "comprising," "includes," "including," "having," and/or "have" are intended to designate the presence of an embodied feature, number, step, element, or a combination thereof, but do not preclude the possibility of the presence or addition of one or more other features, number, step, element, or a combination thereof.

As used herein, singular forms such as "a," "an," and "the" are intended to include the plural forms as well, unless the context clearly indicates otherwise.

As used herein, the terms "use," "using," and "used" may be considered synonymous with the terms "utilize," "utilizing," and "utilized," respectively.

As used herein, expressions such as "at least one of," "one of," and "selected from," when preceding a list of elements, modify the entire list of elements and do not modify the individual elements of the list. For example, the expressions "at least one of a to c," "at least one of a, b or c," and "at least one of a, b and/or c" may indicate only a, only b, only c, both (e.g., simultaneously) a and b, both (e.g., simultaneously) a and c, both (e.g., simultaneously) b and c, all of a, b, and c, or variations thereof.

As used herein, the term "and/or" includes any and all combinations of one or more of the associated listed items.

The term "may" will be understood to refer to "one or more embodiments of the present disclosure," some of which include the described element and some of which exclude that element and/or include an alternate element. Similarly, alternative language such as "or" refers to "one or more embodiments of the present disclosure," each including a corresponding listed item.

It will be understood that when an element is referred to as being "on," "connected to," or "coupled to" another element, it may be directly on, connected, or coupled to the other element or one or more intervening elements may also be present. When an element is referred to as being "directly on," "directly connected to," or "directly coupled to" another element, there are no intervening elements present.

Spatially relative terms, such as "beneath," "below," "lower," "above," "upper," "bottom," "top," and the like, may be used herein for ease of description to describe one element or feature's relationship to another element(s) or feature(s) as illustrated in the drawings. It will be understood that the spatially relative terms are intended to encompass different orientations of the device in use or operation in addition to the orientation depicted in the drawings. For example, if the device in the drawings is turned over, elements described as "below" or "beneath" other elements or features would then be oriented "above" or "over" the other elements or features. Thus, the term "below" may encompass both an orientation of above and below. The device may be otherwise oriented (rotated 90 degrees or at other orientations), and the spatially relative descriptors used herein should be interpreted accordingly.

Unless otherwise defined, all terms (including technical and scientific terms) used herein have the same meaning as commonly understood by those of ordinary skill in the art to which the present disclosure pertains. It is also to be understood that terms defined in commonly used dictionaries should be interpreted as having meanings consistent with meanings in the context of the related art, unless expressly defined herein, and should not be interpreted in an ideal or overly formal sense.

In this context, "consisting essentially of" means that any additional components will not materially affect the chemical, physical, optical or electrical properties of the semiconductor film.

Further, in this specification, the phrase "on a plane," or "plan view," means viewing a target portion from the top, and the phrase "on a cross-section" means viewing a cross-section formed by vertically cutting a target portion from the side.

In the drawing, the thickness of layers, films, panels, regions, etc., are exaggerated for clarity and like reference numerals designate like elements throughout, and duplicative descriptions thereof may not be provided in the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In some embodiments, "layer" as utilized herein includes not only a shape formed on the whole surface when viewed from a plan view, but also a shape formed on a partial surface.

In some embodiments, the average particle diameter may be measured by a method well suitable to those skilled in the art, for example, may be measured by a particle size analyzer, or may be measured by an optical microscope image such as a transmission electron micrograph or a scanning electron micrograph. In some embodiments, it is possible to obtain an average particle diameter value by measuring utilizing a dynamic light scattering method, performing data analysis, counting the number of particles for each particle size range, and calculating from this. Unless otherwise defined, the average particle diameter may refer to the diameter (D50) of particles having a cumulative volume of 50 volume % in the particle size distribution.

Herein, "or" is not to be construed as an exclusive meaning, for example, "A or B" is construed to include A, B, A+B, and/or the like.

As utilized herein, when a definition is not otherwise provided, "substituted" refers to replacement of hydrogen of a compound by a substituent selected from among a deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 fluoroalkyl group, a cyano group, and/or combinations thereof.

As utilized herein, when a definition is not otherwise provided, "substituted" refers to replacement of at least one hydrogen of a substituent or a compound by deuterium, a halogen, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C10 fluoroalkyl group, or a cyano group. In some embodiments, in specific examples of the present disclosure, "substituted" refers to replacement of at least one hydrogen of a substituent or a compound by deuterium, a halogen, a C1 to C20 alkyl group, a C6 to C30 aryl group, a C1 to C10 fluoroalkyl group, or a cyano group. In some embodiments, in specific examples of the present disclosure, "substituted" refers to replacement of at least one hydrogen of a substituent or a compound by deuterium, a halogen, a C1 to C5 alkyl group, a C6 to C18 aryl group, a C1 to C5 fluoroalkyl group, or a cyano group. In some embodiments, in specific examples of the present disclosure, "substituted" refers to replacement of at least one hydrogen of a substituent or a compound by deuterium, a cyano group, a halogen, a methyl group, an ethyl group, a propyl group, a butyl group, a phenyl group, a biphenyl group, a terphenyl group, a trifluoromethyl group, or a naphthyl group.

Expressions such as C1 to C30 refer to that the number of carbon atoms is 1 to 30.

A rechargeable lithium battery may be classified into a lithium ion battery, a lithium ion polymer battery, and a lithium polymer battery depending on kinds of a separator and an electrolyte. It also may be classified to be cylindrical, prismatic, coin-type or kind, pouch-type or kind, and/or the like, depending on shapes. In some embodiments, it may be classified to be bulk type or kind and/or thin film type or kind, depending on sizes. Structures and manufacturing methods for lithium ion batteries pertaining to this disclosure are well suitable in the art.

Herein, a cylindrical rechargeable lithium battery will be exemplarily described as an example of the rechargeable lithium battery. FIG. 1 schematically shows the structure of a rechargeable lithium battery according to one or more embodiments. Referring to FIG. 1, a rechargeable lithium battery 100 according to one or more embodiments includes a battery cell including a positive electrode 114, a negative electrode 112 facing the positive electrode 114, a separator 113 between the positive electrode 114 and the negative electrode 112, and an electrolyte impregnating the positive electrode 114, the negative electrode 112, and the separator 113, a battery case 120 housing the battery cell, and a sealing member 140 sealing the battery case 120.

Hereinafter, an additive for an electrolyte according to one or more embodiments will be described.

The additive according to one or more embodiments of the present disclosure is represented by Chemical Formula 1.

Chemical Formula 1

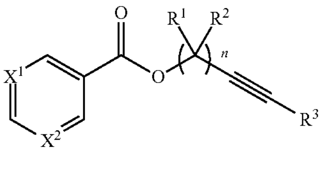

In Chemical Formula 1, $X^1$ and $X^2$ may each independently be N or $CR^a$, at least one of $X^1$ and $X^2$ is N, $R^a$ and $R^1$ to $R^3$ may each independently be hydrogen or a substituted or unsubstituted C1 to C10 alkyl group, and n is one of integers of 1 to 3.

The pyridine or pyrimidine and alkynyl group included in Chemical Formula 1 can capture $PF_5$- as lone pair electron donors. For example, the pyridine, the pyrimidine, or the alkynyl group can capture $PF_5$- alone, or any combination of the pyridine, the pyrimidine, and the alkynyl group can together capture $PF_5$-.

In a rechargeable lithium battery, a non-aqueous electrolyte may decomposed during the initial charge and discharge and thus form a film having passivation ability on the surfaces of positive and negative electrodes. The film may improve storage characteristics at a high temperature but may be deteriorated by acid such as $HF^-$ and $PF_5$- produced by thermal decomposition of lithium salts ($LiPF_6$ and/or the like) which are widely utilized in lithium ion batteries. This acid attack elutes transition metal elements from the positive electrode and thus increases sheet resistance of the electrode due to structural changes of the surface. The acid attack/elution may reduce theoretical capacity due to the loss of the metal elements, which are redox centers, thereby deteriorating expression capacity. For example, the eluted transition metal ions may be electrodeposited on the negative electrode reacting in a strong reduction potential band. The transition metal ions may consume electrons and/or destroy the film during the electrodeposition and expose the surface of the negative electrode, thereby additionally causing the decomposition reaction of an electrolyte. As a result, as the resistance of the negative electrode increases, and irreversible capacity increases, they may cause continuous deterioration of the capacity of a cell. In the present disclosure, the pyridine or pyrimidine and alkynyl group of the additive represented by Chemical Formula 1 (e.g., where at least one of $X^1$ and $X^2$ is N), provide unshared electron pairs to remove acids caused by the decomposition of lithium salts, thereby strengthening an solid-electrolyte-interface (SEI) film on the surface of the negative electrode as well as preventing or reducing deterioration of the SEI film during the high-temperature storage, elution of transition metals at the positive electrode, and/or the like.

In particular, N of the pyridine or pyrimidine may act as a more advantageous or enhanced donor of the unshared electron pairs, when present at a meta position with respect to an acetate group.

As described herein, suppression of the decomposition of the electrolyte and the suppression of side reactions with the electrolyte may be maximized or increased by utilizing the additive with a positive electrode including a cobalt-free lithium nickel manganese oxide, as described elsewhere herein.

For example, n may be one of integers from 1 to 3, and for example, n may be an integer of 1 or 2.

When the n is within the above range, an increase in resistance due to the SEI film thickness may be suppressed or reduced as the alkylene chain between the alkyne and the acetate in Chemical Formula 1 maintains an appropriate or suitable length. For example, $R^1$ to $R^3$ may each independently be hydrogen or a substituted or unsubstituted C1 to C5 alkyl group. For example, $R^3$ may be hydrogen.

In one or more embodiments, the additive represented by Chemical Formula 1 may be selected from among compounds listed in Group 1.

Group 1

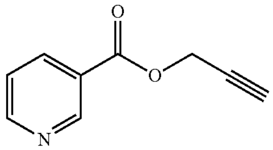

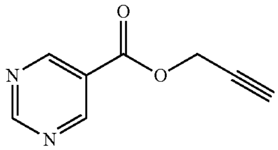

An electrolyte for a rechargeable lithium battery according to another embodiment includes a non-aqueous organic solvent, a lithium salt and the aforementioned additive for an electrolyte.

The additive may be included in an amount of about 0.05 to 5.0 parts by weight based on 100 parts by weight of the electrolyte for the rechargeable lithium battery.

For example, the additive may be included in an amount of about 0.05 to 3.0 parts by weight based on 100 parts by weight of the electrolyte for a rechargeable lithium battery.

When the content (e.g., amount) range of the additive is as described above, it is possible to implement a rechargeable lithium battery having enhanced or improved cycle-life characteristics and output characteristics by preventing or reducing an increase in resistance at high temperatures.

The electrolyte for the rechargeable lithium battery may further include at least one other additive selected from among vinylene carbonate (VC), fluoroethylene carbonate (FEC), difluoroethylene carbonate, chloroethylene carbonate, dichloroethylene carbonate, bromoethylene carbonate, dibromoethylene carbonate, nitroethylene carbonate, cyanoethylene carbonate, vinylethylene carbonate (VEC), adiponitrile (AN), succinonitrile (SN), 1,3,6-hexane tricyanide (HTCN), propenesultone (PST), propanesultone (PS), lithium tetrafluoroborate ($LiBF_4$), lithium difluorophosphate ($LiPO_2F_2$), and 2-fluoro biphenyl (2-FBP).

By further including the aforementioned other additives, the cycle-life may be further enhanced or improved or gases generated from the positive electrode and the negative electrode may be effectively controlled or selected during high-temperature storage.

The other additives may be included in an amount of about 0.2 to 20 parts by weight, specifically about 0.2 to 15 parts by weight, for example, about 0.2 to 10 parts by weight, based on 100 parts by weight of the electrolyte for the rechargeable lithium battery.

When the content (e.g., amount) of other additives is as described above, an increase in film resistance may be minimized or reduced, thereby contributing to the improvement of battery performance.

The non-aqueous organic solvent serves as a medium for transmitting ions taking part in the electrochemical reaction of a battery.

The non-aqueous organic solvent may be a carbonate-based, ester-based, ether-based, ketone-based, alcohol-based, or aprotic solvent.

The carbonate-based solvent may include dimethyl carbonate (DMC), diethyl carbonate (DEC), dipropyl carbonate (DPC), methylpropyl carbonate (MPC), ethylpropyl carbonate (EPC), ethylmethyl carbonate (EMC), ethylene carbonate (EC), propylene carbonate (PC), butylene carbonate (BC), and/or the like. The ester-based solvent may include methyl acetate, ethyl acetate, n-propyl acetate, t-butyl acetate, methylpropionate, ethylpropionate, propylpropionate, decanolide, mevalonolactone, caprolactone, and/or the like. The ether-based solvent may include dibutyl ether, tetraglyme, diglyme, dimethoxyethane, 2-methyltetrahydrofuran, tetrahydrofuran, and/or the like. In some embodiments, the ketone-based solvent may include cyclohexanone, and/or the like. The alcohol-based solvent may include ethanol, isopropyl alcohol, and/or the like and the aprotic solvent may include nitriles such as $R^1$—CN (wherein $R^1$ is a hydrocarbon group having a C2 to C20 linear, branched, or cyclic structure and may include a double bond, an aromatic ring, or an ether bond), and/or the like, dioxolanes such as 1,3-dioxolane, and/or the like, sulfolanes, and/or the like.

The non-aqueous organic solvent may be utilized alone or in a mixture. When the organic solvent is utilized in a mixture, the mixture ratio may be controlled or selected in accordance with a desirable battery performance.

For example, the non-aqueous organic solvent may be composed of only chain carbonate. In one or more embodiments, the non-aqueous organic solvent consists of chain carbonate, or consists essentially of chain carbonate. In these cases, as the resistance increase rate during high-temperature storage is significantly alleviated, excellent or suitable high-temperature storage characteristics can be implemented.

As utilized herein, "be composed of only chain carbonate, consists of chain carbonate, or consists essentially of chain carbonate," refers to organic solvents (e.g., non-aqueous organic solvents) that belong to the category of chain carbonates, either alone or in combination, are included without mixing with (i.e., excluding) cyclic carbonates and/or the like.

As a specific example, the chain carbonate may be represented by Chemical Formula 2.

Chemical Formula 2

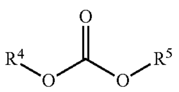

In Chemical Formula 2

$R^4$ and $R^5$ may each independently be a substituted or unsubstituted C1 to C20 alkyl group.

For example, $R^4$ and $R^5$ of Chemical Formula 2 may each independently be a substituted or unsubstituted C1 to C10 alkyl group, and for example $R^4$ and $R^5$ may each independently be a substituted or unsubstituted C1 to C5 alkyl group.

In an example embodiment, $R^4$ and $R^5$ of Chemical Formula 2 may each independently be a substituted or unsubstituted methyl group, a substituted or unsubstituted ethyl group, a substituted or unsubstituted n-propyl group, a substituted or unsubstituted n-butyl group, a substituted or unsubstituted n-pentyl group, a substituted or unsubstituted iso-butyl group, or a substituted or unsubstituted neo-pentyl group.

For example, the non-aqueous organic solvent according to a specific embodiment may be at least two selected from among dimethyl carbonate (DMC), diethyl carbonate (DEC), dipropyl carbonate (DPC), methylpropyl carbonate (MPC), ethylpropyl carbonate (EPC), and ethylmethyl carbonate (EMC).

The non-aqueous organic solvent according to the most specific embodiment may be a mixed solvent of dimethyl carbonate (DMC) and ethylmethyl carbonate (EMC).

The non-aqueous organic solvent may further include an aromatic hydrocarbon-based organic solvent in addition to the carbonate-based solvent. Herein, the carbonate-based solvent and the aromatic hydrocarbon-based organic solvent may be mixed in a volume ratio of about 1:1 to about 30:1.

The aromatic hydrocarbon-based organic solvent may be an aromatic hydrocarbon-based compound of Chemical Formula 3.

Chemical Formula 3

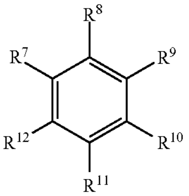

In Chemical Formula 3, $R^7$ to $R^{12}$ may each independently be the same or different and are selected from among hydrogen, a halogen, a C1 to C10 alkyl group, a C1 to C10 haloalkyl group, and/or a combination thereof.

Specific examples of the aromatic hydrocarbon-based organic solvent may be selected from among benzene, fluorobenzene, 1,2-difluorobenzene, 1,3-difluorobenzene, 1,4-difluorobenzene, 1,2,3-trifluorobenzene, 1,2,4-trifluorobenzene, chlorobenzene, 1,2-dichlorobenzene, 1,3-dichlorobenzene, 1,4-dichlorobenzene, 1,2,3-trichlorobenzene, 1,2,4-trichlorobenzene, iodobenzene, 1,2-diiodobenzene, 1,3-diiodobenzene, 1,4-diiodobenzene, 1,2,3-triiodobenzene, 1,2,4-triiodobenzene, toluene, fluorotoluene, 2,3-difluorotoluene, 2,4-difluorotoluene, 2,5-difluorotoluene, 2,3,4-trifluorotoluene, 2,3,5-trifluorotoluene, chlorotoluene, 2,3-dichlorotoluene, 2,4-dichlorotoluene, 2,5-dichlorotoluene, 2,3,4-trichlorotoluene, 2,3,5-trichlorotoluene, iodotoluene, 2,3-diiodotoluene, 2,4-diiodotoluene, 2,5-diiodotoluene, 2,3,4-triiodotoluene, 2,3,5-triiodotoluene, xylene, and/or a combination thereof.

The lithium salt dissolved in the non-organic solvent supplies lithium ions in a battery, enables a basic operation of a rechargeable lithium battery, and improves transportation of the lithium ions between positive and negative electrodes. Examples of the lithium salt include at least one selected from among $LiPF_6$, $LiBF_4$, $LiSbF_6$, $LiAsF_6$, $LiN(SO_2C_2F_5)_2$, $Li(CF_3SO_2)_2N$, $LiN(SO_3C_2F_5)_2$, $Li(FSO_2)_2N$ (lithium bis(fluorosulfonyl)imide:LiFSI), $LiC_4F_9SO_3$, $LiClO_4$, $LiAlO_2$, $LiAlCl_4$, $LiPO_2F_2$, $LiN(C_xF_{2x+1}SO_2)(C_yF_{2y+1}SO_2)$, wherein x and y are natural numbers, for example an integer in a range of 1 to 20, LiCl, LiI, $LiB(C_2O_4)_2$ (lithium bis(oxalato) borate: LiBOB), LiDFOB (lithium difluoro(oxalato)borate), and $Li[PF_2(C_2O_4)_2]$ (lithium difluoro (bis oxalato) phosphate). The lithium salt may be utilized in a concentration in a range of about 0.1 M to about 2.0 M. When the lithium salt is included at the above concentration range, an electrolyte may have excellent or suitable performance and lithium ion mobility due to optimal or suitable electrolyte conductivity and viscosity.

Another embodiment provides a rechargeable lithium battery including a positive electrode including a positive electrode active material; a negative electrode including a negative electrode active material; and the aforementioned electrolyte.

The positive electrode includes a positive electrode current collector and a positive electrode active material layer on the positive electrode current collector, and the positive electrode active material layer includes a positive electrode active material.

The positive electrode active material may include a cobalt-free lithium nickel manganese oxide.

In the present disclosure, the cobalt-free lithium nickel manganese-based oxide as a positive electrode active material refers to a positive electrode active material including (e.g., composed mainly or substantially of) nickel, manganese, etc. without including (e.g., excluding) cobalt (e.g., without any cobalt as an active component) in the composition of the positive electrode active material.

For example, the cobalt-free lithium nickel manganese-based oxide may include at least one type or kind of lithium composite oxide(s) represented by Chemical Formula 4.

Chemical Formula 4

$$Li_aNi_xMn_yM1_zM2_wO_{2\pm b}X_c$$

In Chemical Formula 4, $0.9\leq a<1.2$, $0\leq b<0.1$, $0\leq c<0.1$, $0\leq w<0.1$, $0.6\leq x\leq 1.0$, $0<y<0.4$, $0<z<0.1$, $w+x+y+z=1$, M1 and M2 may each independently be at least one element selected from among Al, Mg, Ti, Zr, Cr, Sr, V, B, W, Mo, Nb, Si, Ba, Ca, Ce, Cr, Fe, and Nb, and X is at least one element selected from among S, F, P, and Cl.

The lithium composite oxide(s) may have a coating layer on the surface, or may be mixed with another lithium composite oxide having a coating layer. The coating layer may include at least one coating element compound selected from among an oxide of a coating element, a hydroxide of a coating element, an oxyhydroxide of a coating element, an oxycarbonate of a coating element, and a hydroxy carbonate of a coating element. The compound for the coating layer may be amorphous or crystalline. The coating element included in the coating layer may include Mg, Al, Co, K, Na, Ca, Si, Ti, V, Sn, Ge, Ga, B, As, Zr, or a mixture thereof. The coating layer may be formed or disposed in a method having no adverse influence on properties of a positive electrode active material by utilizing these elements in the compound. For example, the method may include any coating method (e.g., spray coating, dipping, etc.), suitable in the related art or field.

For example, Chemical Formula 4 may be represented by Chemical Formula 4-1.

Chemical Formula 4-1

$$Li_aNi_{x1}Mn_{y1}Al_{z1}M2_{w1}O_{2\pm b}X_c$$

In Chemical Formula 4-1, $0.9\leq a<1.2$, $0\leq b<0.1$, $0\leq c<0.1$, $0\leq w1<0.1$, $0.6\leq x1<1.0$, $0<y1<0.4$, $0<z1<0.1$, $w1+x1+y1+z1=1$, M2 is an element selected from among Mg, Ti, Zr, Cr, Sr, V, B, W, Mo, Nb, Si, Ba, Ca, Ce, Cr, Fe, and Nb, and X is at least one element selected from among S, F, P, and Cl.

In Chemical Formula 4-1, x1 may be $0.6\leq x1\leq 0.79$, y1 may be $0.2\leq y1\leq 0.39$, and z1 may be $0.01\leq z1<0.1$.

The positive electrode active material may be included in an amount of about 90 wt % to about 98 wt % based on a total weight of a positive electrode active material layer.

Each content (e.g., amount) of the conductive material and binder may be about 1 wt % to about 5 wt % based on a total weight of a positive electrode active material layer The positive electrode active material layer further includes a conductive material and a binder.

The conductive material is included to provide the positive electrode conductivity and any electrically conductive material may be utilized as a conductive material unless it causes a chemical change. Examples of the conductive material include a carbon-based material such as natural graphite, artificial graphite, carbon black, acetylene black, ketjen black, a carbon fiber, and/or the like; a metal-based material of a metal powder or a metal fiber including copper, nickel, aluminum silver, and/or the like; a conductive polymer such as a polyphenylene derivative; or a mixture thereof.

The binder improves binding properties of positive electrode active material particles with one another and with a current collector. Examples thereof may be polyvinyl alcohol, carboxylmethyl cellulose, hydroxypropyl cellulose, diacetyl cellulose, polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, a styrene-butadiene rubber, an acrylated styrene-butadiene rubber, an epoxy resin, nylon, and/or the like, but is not limited thereto.

Al (aluminum) may be utilized as the positive electrode current collector, but is not limited thereto.

The negative electrode includes a negative electrode current collector and a negative electrode active material layer including a negative electrode active material formed on the negative electrode current collector.

The negative electrode active material may include a material that reversibly intercalates/deintercalates lithium ions, a lithium metal, a lithium metal alloy, a material capable of doping/dedoping lithium, and/or transition metal oxide.

The material that reversibly intercalates/deintercalates lithium ions may include a carbon material. The carbon material may be any generally-utilized carbon-based negative electrode active material in a rechargeable lithium battery. Examples thereof may be crystalline carbon, amorphous carbon, or a mixture thereof. The crystalline carbon may be irregular, or sheet, flake, spherical, and/or fiber shaped natural graphite and/or artificial graphite. The amorphous carbon may be a soft carbon, a hard carbon, a mesophase pitch carbonization product, calcined coke, and/or the like.

The lithium metal alloy includes an alloy of lithium and a metal selected from among Na, K, Rb, Cs, Fr, Be, Mg, Ca, Sr, Si, Sb, Pb, In, Zn, Ba, Ra, Ge, Al, and Sn.

The material capable of doping/dedoping lithium may be Si, Si—C composite, $SiO_x$ (0<x<2), a Si-Q alloy wherein Q is an element selected from among an alkali metal, an alkaline-earth metal, a Group 13 element, a Group 14 element except Si, a Group 15 element, a Group 16 element, a transition metal, a rare earth element, and a combination thereof), Sn, $SnO_2$, a Sn—$R^{11}$ alloy (wherein $R^{11}$ is an element selected from among an alkali metal, an alkaline-earth metal, a Group 13 element, a Group 14 element except Sn, a Group 15 element, a Group 16 element, a transition metal, a rare earth element, and a combination thereof,), and/or the like. At least one of these materials may be mixed with $SiO_2$.

The elements Q and $R^{11}$ may be selected from among Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, TI, Ge, P, As, Sb, Bi, S, Se, Te, Po, and a combination thereof.

The transition metal oxide may be vanadium oxide, lithium vanadium oxide, or lithium titanium oxide.

In one or more embodiments, the negative electrode active material may include at least one selected from among graphite and a Si composite.

The Si composite may include a core including Si-based particles and an amorphous carbon coating layer, and for example, the Si-based particles may include at least one of Si particles, Si composites, $SiO_x$ ($0<x\leq 2$), and an Si alloy.

For example, a void may be included in the center portion of the core including the Si-based particles, and a radius of the center portion corresponds to 30% to 50% of the radius of the Si composite. An average particle diameter of the Si composite may be about 5 μm to about 20 μm, and an average particle diameter of the Si-based particles may be about 10 nm to about 200 nm As utilized herein, the average particle diameter may be the particle size (D50) at 50 volume % in a cumulative size-distribution curve.

When the Si-based particles have an average particle diameter within the range, volume expansion during the charge and discharge may be suppressed or reduced, and interruption of a conductive path due to particle crushing during the charge and discharge may be prevented or reduced.

The core including the Si-based particles may further include amorphous carbon, wherein the center portion may not include (e.g., may exclude) amorphous carbon, and the amorphous carbon may be present only on the surface portion of the Si composite.

Herein, the surface portion indicates a region from the center portion of the negative electrode active material to the outermost surface of the Si composite.

In one or more embodiments, the Si-based particles are substantially uniformly included over the Si composite, that is, present at a substantially uniform concentration in the center portion and the surface portion thereof.

The amorphous carbon may be soft carbon, hard carbon, mesophase pitch carbonized product, calcined coke, or a combination thereof.

For example, the Si—C composite may include Si particles and crystalline carbon.

The Si particles may be included in an amount of about 1 wt % to about 60 wt %, for example, about 3 wt % to about 60 wt %, based on a total weight of the Si—C composite.

The crystalline carbon may be for example graphite, and, for example, natural graphite, artificial graphite, or a combination thereof.

An average particle diameter of the crystalline carbon may be about 5 μm to about 30 μm.

When the negative electrode active material includes graphite and Si composite together, the graphite and Si composite may be included as a mixture, wherein the graphite and Si—C composite may be included in a weight ratio of about 99:1 to about 50:50.

In one or more embodiments, the graphite and Si composite may be included in a weight ratio of about 97:3 to about 80:20, or about 95:5 to about 80:20.

A precursor of the amorphous carbon may include a coal-based pitch, mesophase pitch, petroleum-based pitch, coal-based oil, petroleum-based heavy oil, or a polymer resin such as a phenol resin, a furan resin, or a polyimide resin.

In the negative electrode active material layer, the negative electrode active material may be included in an amount of about 95 wt % to about 99 wt % based on a total weight of the negative electrode active material layer.

The negative electrode active material layer includes a binder, and optionally a conductive material. In the negative electrode active material layer, a content (e.g., amount) of the binder may be about 1 wt % to about 5 wt % based on a total weight of the negative electrode active material layer. When the negative electrode active material layer includes a conductive material, the negative electrode active material layer includes about 90 wt % to about 98 wt % of the negative electrode active material, about 1 wt % to about 5 wt % of the binder, and about 1 wt % to about 5 wt % of the conductive material.

The binder improves binding properties of negative electrode active material particles with one another and with a current collector. The binder includes a non-water-soluble binder, a water-soluble binder, or a combination thereof.

The non-water-soluble binder may be selected from among polyvinylchloride, carboxylated polyvinylchloride, polyvinylfluoride, polyurethane, polytetrafluoroethylene, polyvinylidene fluoride, polyethylene, polypropylene, polyamideimide, polyimide, or a combination thereof.

The water-soluble binder may be a rubber-based binder or a polymer resin binder. The rubber-based binder may be selected from among a styrene-butadiene rubber, an acrylated styrene-butadiene rubber (SBR), an acrylonitrile-butadiene rubber, an acrylic rubber, a butyl rubber, a fluorine rubber, and a combination thereof. The polymer resin binder may be selected from among polytetrafluoroethylene, ethylenepropylenecopolymer, polyethyleneoxide, polyvinylpyrrolidone, polyepichlorohydrine, polyphosphazene, polyacrylonitrile, polystyrene, an ethylenepropylenediene copolymer, polyvinylpyridine, chlorosulfonated polyethylene, latex, a polyester resin, an acrylic resin, a phenolic resin, an epoxy resin, polyvinyl alcohol, and a combination thereof.

When the water-soluble binder is utilized as a negative electrode binder, a cellulose-based compound may be further utilized to provide viscosity as a thickener. The cellulose-based compound includes one or more of carboxymethyl cellulose, hydroxypropylmethyl cellulose, methyl cellulose, or alkali metal salts thereof. The alkali metal may be Na, K, or Li. Such a thickener may be included in an amount of about 0.1 to about 3 parts by weight based on 100 parts by weight of the negative electrode active material.

The conductive material is included to provide electrode conductivity and any electrically conductive material may be utilized as a conductive material unless it causes a chemical change. Examples of the conductive material include a carbon-based material such as natural graphite, artificial graphite, carbon black, acetylene black, ketjen black, a carbon fiber, and/or the like; a metal-based material of a metal powder or a metal fiber including copper, nickel, aluminum silver, and/or the like; a conductive polymer such as a polyphenylene derivative; or a mixture thereof.

The negative electrode current collector may include one selected from among a copper foil, a nickel foil, a stainless steel foil, a titanium foil, a nickel foam, a copper foam, a polymer substrate coated with a conductive metal, and a combination thereof.

The rechargeable lithium battery may further include a separator between the negative electrode and the positive electrode, depending on a type or kind of the rechargeable lithium battery. Such a separator may be a porous substrate or a composite porous substrate.

The porous substrate may be a substrate including pores, and lithium ions may move through the pores. Examples of the porous substrate include polyethylene, polypropylene, polyvinylidene fluoride, and multi-layers thereof such as a polyethylene/polypropylene double-layered separator, a polyethylene/polypropylene/polyethylene triple-layered separator, and a polypropylene/polyethylene/polypropylene triple-layered separator.

The composite porous substrate may have a form including a porous substrate and a functional layer on the porous substrate. The functional layer may be, for example, at least one of a heat-resistant layer and an adhesive layer from the viewpoint of enabling additional function. For example, the heat-resistant layer may include a heat-resistant resin and optionally a filler.

In some embodiments, the adhesive layer may include an adhesive resin and optionally a filler.

The filler may be an organic filler or an inorganic filler.

The rechargeable lithium battery may have a charging upper limit voltage of greater than or equal to about 4.45 V. For example, the charging upper limit voltage may be about 4.45 V to about 4.55 V.

Terms such as "substantially," "about," and "approximately" are used as relative terms and not as terms of degree, and are intended to account for the inherent deviations in measured or calculated values that would be recognized by those of ordinary skill in the art. They may be inclusive of the stated value and an acceptable range of deviation as determined by one of ordinary skill in the art, considering the limitations and error associated with measurement of that quantity. For example, "about" may refer to one or more standard deviations, or ±30%, 20%, 10%, 5% of the stated value.

Numerical ranges disclosed herein include and are intended to disclose all subsumed sub-ranges of the same numerical precision. For example, a range of "1.0 to 10.0" includes all subranges having a minimum value equal to or greater than 1.0 and a maximum value equal to or less than 10.0, such as, for example, 2.4 to 7.6. Applicant therefore reserves the right to amend this specification, including the claims, to expressly recite any sub-range subsumed within the ranges expressly recited herein.

In the present disclosure, when particles are spherical, "diameter" indicates an average particle diameter, and when the particles are non-spherical, the "diameter" indicates a major axis length. The diameter (or size) of the particles may be measured by particle size analysis, dynamic light scattering, scanning electron microscopy, and/or transmission electron microscope photography. When the size of the particles is measured utilizing a particle size analyzer, the average particle diameter (or size) may be referred to as D50. The term "D50" as utilized herein refers to the average diameter (or size) of particles whose cumulative volume corresponds to 50 vol % in the particle size distribution (e.g., cumulative distribution), and refers to the value of the particle size corresponding to 50% from the smallest particle when the total number of particles is 100% in the distribution curve accumulated in the order of the smallest particle size to the largest particle size. Particle size analysis may be performed with a HORIBA LA-950 laser particle size analyzer.

Hereinafter, examples of the present disclosure and comparative examples are described. These examples, however, are not in any sense to be interpreted as limiting the scope of the present disclosure.

EXAMPLES

Synthesis Example: Synthesis of Additives

Synthesis Example 1: Synthesis of Chemical Formula 1a

Reaction Scheme 1

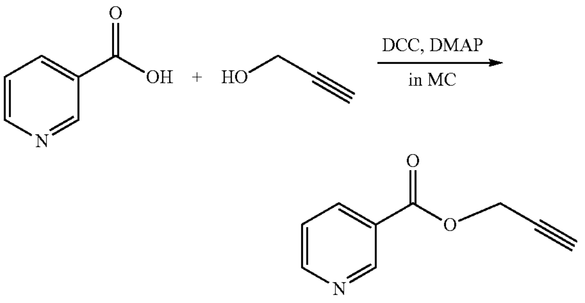

1a

Nicotinic acid is first contacted with (e.g., reacted in) DCC (N,N'-dicyclohexylcarbodiimide), and DMAP (4-dimethylaminopyridine) in MC (dichloromethane) for 30 minutes. Herein, propargyl alcohol is slowly dropped thereinto under an N2 charging environment.

After filtering the mixture and removing solvents from a filtrate therefrom, the residue is silica-filtered, obtaining a compound represented by Chemical Formula 1a.

Comparative Synthesis Example 1: Synthesis of Chemical Formula C1

A compound represented by Chemical Formula C1 is obtained in substantially the same manner as in Synthesis Example 1 except that the nicotinic acid is replaced with pyridine-2-carboxylic acid.

Chemical Formula C1

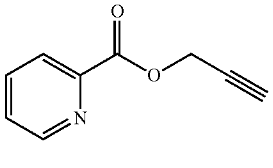

Comparative Synthesis Example 2: Synthesis of Chemical Formula C2

A compound represented by Chemical Formula C2 is obtained in substantially the same manner as in Synthesis Example 1 except that the nicotinic acid is replaced with isonicotinic acid.

Chemical Formula C2

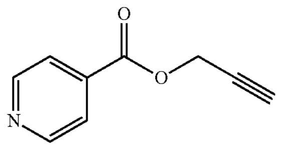

Example: Manufacture of Rechargeable Lithium Battery

Example 1

$LiNi_{0.75}Mn_{0.23}Al_{0.02}O_2$ as a positive electrode active material, polyvinylidene fluoride as a binder, and acetylene black as a conductive material were mixed in a weight ratio of 96:3:1 and then, dispersed in N-methyl pyrrolidone, preparing positive electrode active material slurry.

The positive electrode active material slurry was coated on a 15 μm-thick Al foil, dried at 100° C., and pressed, manufacturing a positive electrode.

Negative electrode active material slurry was also prepared by utilizing a mixture of artificial graphite and Si—C composite in a weight ratio of 93:7 as a negative electrode current collector and then, mixing the negative electrode current collector, a styrene-butadiene rubber binder, and carboxylmethyl cellulose in a weight ratio of 98:1:1 and dispersing the obtained mixture in distilled water.

As for the Si—C composite, a core including artificial graphite and silicon particles was coated with coal-based pitch on the surface.

The negative electrode active material slurry was coated on a 10 μm-thick Cu foil, dried at 100° C., and pressed, manufacturing a negative electrode.

The manufactured positive and negative electrodes were assembled with a 10 μm-thick polyethylene separator to manufacture an electrode assembly, and an electrolyte was injected thereinto, manufacturing a rechargeable lithium battery cell.

The electrolyte had a following composition.

Composition of Electrolyte

Salt: 1.5 M $LiPF_6$

Solvent: ethylene carbonate: ethylmethyl carbonate:dimethyl carbonate (EC:EMC:DMC=a volume ratio of 20:10:70)

Additive: 0.25 parts by weight of the compound represented by Chemical Formula 1a, 10 parts by weight of fluoroethylenecarbonate (FEC), and 0.5 parts by weight of succinonitrile (SN)

However, in the above composition of the electrolyte, "parts by weight" refers to the relative weight of the additive based on 100 weight of the total electrolyte excluding (i.e., except) the additive, (i.e., "total electrolyte" equals the sum of the lithium salt+the non-aqueous organic solvent).

Examples 2 and 3

Rechargeable lithium battery cells were manufactured in substantially the same manner as in Example 1 except that the content (e.g., amount) of the compound represented by Chemical Formula 1a was changed, respectively, to 0.5 parts by weight and 1.0 part by weight.

Examples 4 to 6

Rechargeable lithium battery cells were manufactured in substantially the same manner as in Examples 1 to 3 except that the electrolyte was prepared with (by utilizing) a solvent including ethylmethyl carbonate (EMC) and dimethyl carbonate (DMC) at a volume ratio of ethylmethyl carbonate (EMC):dimethyl carbonate (DMC) of 60:40.

Comparative Example 1

A rechargeable lithium battery cell was manufactured in substantially the same manner as in Example 1 except that an electrolyte including no additive was utilized.

Comparative Examples 2 and 3

Rechargeable lithium battery cells are manufactured in substantially the same manner as in Example 1 except that the compound represented by Chemical Formula C1 and the compound represented by Chemical Formula C2, respectively, were utilized as the additive instead of the compound represented by Chemical Formula 1a.

Each composition of the additives for an electrolyte according to Examples 1 to 6 and Comparative Examples 1 to 3 is shown in Table 1.

TABLE 1

| | | Other additives | | | | |
|---|---|---|---|---|---|---|
| | Additive (parts by weight) | FEC (parts by weight) | SN (parts by weight) | Solvent (volume ratio) | | |
| | | | | EC | EMC | DMC |
| Example 1 | Chemical Formula 1a (0.25) | 10 | 0.5 | 20 | 10 | 70 |
| Example 2 | Chemical Formula 1a (0.5) | 10 | 0.5 | 20 | 10 | 70 |
| Example 3 | Chemical Formula 1a (1.0) | 10 | 0.5 | 20 | 10 | 70 |
| Example 4 | Chemical Formula 1a (0.25) | 10 | 0.5 | — | 60 | 40 |
| Example 5 | Chemical Formula 1a (0.5) | 10 | 0.5 | — | 60 | 40 |
| Example 6 | Chemical Formula 1a (1.0) | 10 | 0.5 | — | 60 | 40 |
| Comparative Example 1 | — | 10 | 0.5 | 20 | 10 | 70 |
| Comparative Example 2 | Chemical Formula C1 (0.25) | 10 | 0.5 | 20 | 10 | 70 |
| Comparative Example 3 | Chemical Formula C2 (0.25) | 10 | 0.5 | 20 | 10 | 70 |

Evaluation 1: Evaluation of CV Characteristics

Figure 2:
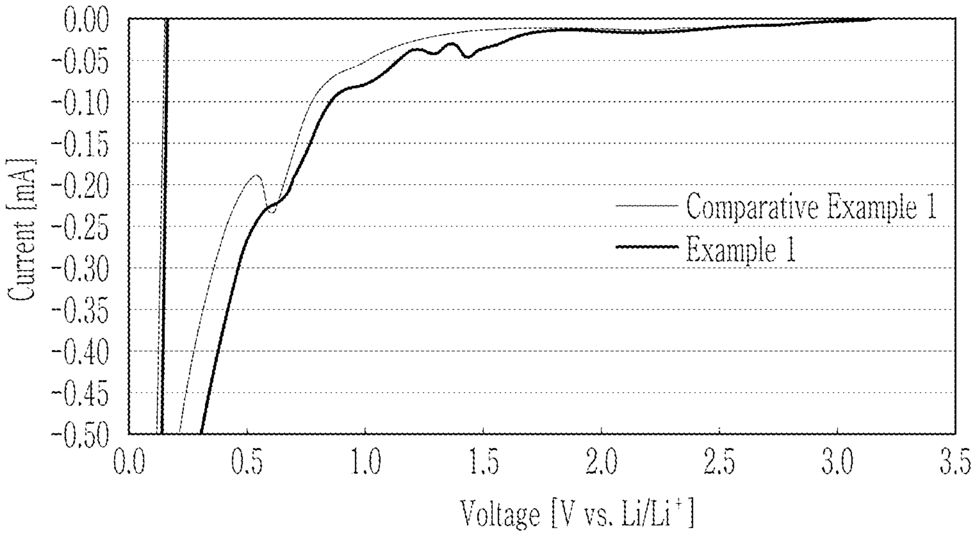
FIG. 2 is a graph showing the results of the negative electrode cyclic voltammetry (CV) of the electrolyte at room temperature prepared in an example according to one or more embodiments of the present disclosure and a comparative example.

In order to evaluate electrochemical stability of the electrolytes according to Comparative Example 1 and Example 1, cyclic voltammetry (CV) was measured, and the results are shown in FIG. 2.

A three-electrode electrochemical cell utilizing a graphite negative electrode as a working electrode and Li metal as a reference electrode and a counter electrode was utilized to measure negative electrode cyclic voltammetry (CV). Herein, the scan was performed for three cycles from 3 V to 0 V and from 0 V to 3 V at a scan speed of 0.1 mV/sec.

FIG. 2 is a graph showing the results of the negative electrode cyclic voltammetry (CV) of the electrolyte at room temperature according to Example 1 and Comparative Example 1.

As shown in FIG. 2, the electrolyte of Example 1 including the additive according to the present disclosure exhibited a reduction decomposition peak at about 1.0 V or more.

In contrast, the electrolyte including no additive according to Comparative Example 1 exhibited a reduction decomposition peak at a lower potential.

This should show or prove that the electrolyte including the additive according to an example embodiment of the present disclosure interacted with a solvent at a relatively high reduction potential, and accordingly, the electrolyte according to Example 1 is configured to form an initial SEI film on the negative electrode over a wide voltage range before the solvent decomposition during the charge in which lithium ions were inserted into the negative electrode. According, compared with the rechargeable lithium battery cell adopting the electrolyte of Comparative Example 1 forming no initial SEI film, the rechargeable lithium battery cell adopting the electrolyte of Example 1 is configured or designed to exhibit excellent or suitable battery performance.

Evaluation 2: Evaluation of Room-Temperature Charge/Discharge Cycle Characteristics The rechargeable lithium battery cells according to Examples 1 to 6 and Comparative Examples 1 to 3 were charged and discharged and then, cycle characteristics were measured, and the results are shown in Table 2.

The cells were charged and discharged for 200 cycles under conditions of 0.33 C charge (CC/CV, 4.45 V, 0.025 C cut-off)/1.0 C discharge (CC, 2.5 V cut-off) at 25° C. and then, a capacity retention rate and a change of direct current internal resistance (DC-IR) were measured.

DC-IR is calculated according to Equations 1 and 2, based on a voltage changed by applying a current of SOC 50 C (a state of being charged to 50% of charge capacity, when a total charge capacity is 100%), to the cells for 30 seconds, and the results are shown in Table 2.

$$\text{Capacity retention rate} = (\text{capacity after 200th cycles}/\text{capacity after 1st cycle}) * 100 \qquad \text{Equation 1}$$

$$DC \text{ internal resistance change} = \{(DC\text{-IR after 200th cycles} - DC\text{-IR after 1st cycle})/(DC\text{-IR after 1st cycle})\} * 100 \qquad \text{Equation 2}$$

TABLE 2

| | Capacity retention rate (@25° C., 200 Cycle) | Initial resistance @25° C. (mΩ) | DC-IR after 200th cy @25° C. (mΩ) | DC-IR change rate after 200th cy @25° C. (%) |
|---|---|---|---|---|
| Comparative Example 1 | 87.1 | 41 | 84.5 | 206% |
| Comparative Example 2 | 88.4 | 43.2 | 84.1 | 195% |
| Comparative Example 3 | 88.2 | 43.1 | 84.5 | 196% |
| Example 1 | 89.8 | 42.8 | 83.4 | 195% |
| Example 2 | 91.5 | 43.3 | 82.7 | 191% |
| Example 3 | 89.9 | 42.9 | 85.7 | 200% |
| Example 4 | 91.7 | 43.4 | 84.2 | 194% |
| Example 5 | 92.2 | 43.8 | 83.8 | 191% |
| Example 6 | 91.1 | 44.1 | 86.3 | 196% |

Referring to Table 2, when the additive according to the present disclosure is utilized, room-temperature cycle-life characteristics are improved.

Evaluation 3: Evaluation of High-Temperature (45° C.) Cycle-Life Characteristics The rechargeable lithium battery cells according to Examples 1 to 6 and Comparative Examples 1 to 3 were are charged and discharged for 200 cycles under conditions of 0.33 C charge (CC/CV, 4.45 V, 0.025 C cut-off)/1.0 C discharge (CC, 2.5 V cut-off) at 45° C. and then, a capacity retention rate and a change in direct current internal resistance (DC-IR) were measured.

DC-IR is calculated according to Equations 1 and 2 based on a voltage changed while the cells are discharged by applying a current of SOC 50 C for 30 seconds, and the results are shown in Table 3.

TABLE 3

| | Capacity retention rate (@45° C., 200 Cycles) | Initial resistance @45° C. (mΩ) | DC-IR after 200th cy @45° C. (mΩ) | DC-IR change rate after 200th cy @45° C. (%) |
|---|---|---|---|---|
| Comparative Example 1 | 85.0 | 47.6 | 106.3 | 223 |
| Comparative Example 2 | 86.0 | 51.2 | 110.0 | 215 |
| Comparative Example 3 | 86.1 | 49.6 | 108.0 | 218 |
| Example 1 | 87.7 | 49.4 | 105.2 | 213 |
| Example 2 | 89.4 | 49.9 | 104.5 | 209 |
| Example 3 | 87.8 | 49.5 | 107.5 | 217 |
| Example 4 | 89.6 | 50 | 106 | 212 |
| Example 5 | 90.1 | 50.4 | 105.6 | 210 |
| Example 6 | 89.0 | 50.7 | 108.1 | 213 |

Referring to Table 3, when the additive according to the present disclosure is utilized, high-temperature cycle-life characteristics are improved.

Evaluation 4: Evaluation of High-Temperature Storage Characteristics (Capacity Retention Rate/Capacity Recovery Rate/DC-IR)

The rechargeable lithium battery cells according to Examples 1 to 6 and Comparative Examples 1 to 3 were once charged and discharged at 0.33 C and then, charge and discharge capacity (before storage at a high temperature) was measured.

The rechargeable lithium battery cells according to Examples 1 to 6 and Comparative Examples 1 to 3 were charged to SOC 100% (a state of being charged to 100% of charge capacity, when a total charge capacity is 100%), stored at 60° C. for 30 days, and discharged to 3.0 V at 0.33 C under a constant current condition and then, initial discharge capacity was measured.

The cells were recharged at 0.33 C to 4.3 V under a constant current and cut off at 0.02 C under a constant voltage condition, and discharged at 0.33 C to 3.0 V under the constant current condition and then, discharge capacity was twice measured. A ratio of first discharge capacity to the initial discharge capacity is shown as a capacity retention rate (retention capacity), and a second discharge capacity is shown as a capacity recovery rate (recovery capacity).

For the rechargeable lithium battery cells according to Examples 1 to 6 and Comparative Examples 1 to 3, initial DC resistance (DCIR) as ΔV/ΔI (change in voltage/change in current) was measured, and after changing a maximum energy state inside the battery cells into a full charge state (SOC 100%) and storing the cells in this state at a high temperature (60° C.) for 30 days, DC resistance was measured to calculate a DCIR increase rate (%) according to Equation 3, and the results are shown in Table 4.

Equation 3

$$DCIR\text{ Increase rate} = (DCIR\text{ after 30th days/initial }DCIR) * 100$$

TABLE 4

| | Capacity retention rate (@60° C., 300D) | Capacity recovery rate (@60° C., 300D) | Initial resistance (@25° C., mΩ) | DC-IR @ 60° C., 30D (mΩ) | DC-IR change rate (%) |
|---|---|---|---|---|---|
| Comparative Example 1 | 86.2 | 89.6 | 41 | 96.3 | 235 |
| Comparative Example 2 | 87.1 | 90.4 | 42.5 | 97.7 | 230 |
| Comparative Example 3 | 87.8 | 91 | 42.5 | 96.9 | 228 |
| Example 1 | 88.9 | 92.3 | 42.8 | 95.2 | 222 |
| Example 2 | 90.6 | 94 | 43.3 | 94.5 | 218 |
| Example 3 | 89 | 92.4 | 42.9 | 97.5 | 227 |
| Example 4 | 90.8 | 94.2 | 43.4 | 96 | 221 |
| Example 5 | 91.3 | 94.7 | 43.8 | 95.6 | 218 |
| Example 6 | 90.2 | 93.6 | 44.1 | 98.1 | 222 |

Referring to Table 4, the rechargeable lithium battery cells according to Examples 1 to 6, compared with Comparative Examples 1 to 3, each exhibit an improved capacity retention rate and capacity recovery rate but a suppressed or reduced resistance change rate during the high-temperature storage.

While this present disclosure has been described in connection with what is presently considered to be practical example embodiments, it is to be understood that the present disclosure is not limited to the disclosed embodiments, but, on the contrary, is intended to cover one or more suitable modifications and equivalent arrangements included within the spirit and scope of the appended claims and equivalents thereof.

DESCRIPTION OF SYMBOLS

100: rechargeable lithium battery

112: negative electrode

113: separator

114: positive electrode

120: battery case

140: sealing member

What is claimed is:

1. An additive for an electrolyte represented by Chemical Formula 1:

Chemical Formula 1

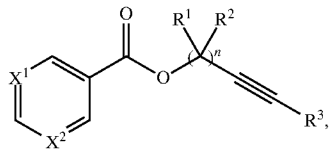

wherein, in Chemical Formula 1, $X^1$ and $X^2$ are each independently N or $CR^a$, at least one selected from among $X^1$ and $X^2$ is N, $R^a$ and $R^1$ to $R^3$ are each independently hydrogen or a substituted or unsubstituted C1 to C10 alkyl group, and n is one of integers of 1 to 3.

2. The additive of claim 1, wherein n is an integer of 1 or 2.

3. The additive of claim 1, wherein $R^1$ to $R^3$ are each independently hydrogen or a substituted or unsubstituted C1 to C5 alkyl group.

4. The additive of claim 1, wherein $R^3$ is hydrogen.

5. The additive of claim 1, wherein the additive is one selected from among compounds of Group 1:

Group 1

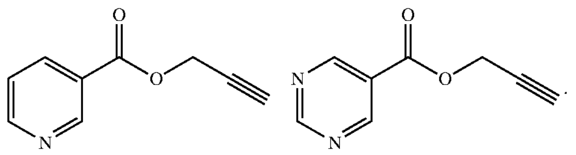

6. An electrolyte for a rechargeable lithium battery, comprising a non-aqueous organic solvent, a lithium salt, and the additive of claim 1.

7. The electrolyte of claim 6, wherein the additive is in an amount of about 0.05 to 5.0 parts by weight based on 100 parts by weight of the electrolyte.

8. The electrolyte of claim 6, wherein the additive is in an amount of about 0.05 to 3.0 parts by weight based on 100 parts by weight of the electrolyte.

9. The electrolyte of claim 6, wherein the electrolyte further comprises at least one other additive selected from among vinylene carbonate (VC), fluoroethylene carbonate (FEC), difluoroethylene carbonate, chloroethylene carbonate, dichloroethylene carbonate, bromoethylene carbonate, dibromoethylene carbonate, nitroethylene carbonate, cyanoethylene carbonate, vinylethylene carbonate (VEC), adiponitrile (AN), succinonitrile (SN), 1,3,6-hexane tricyanide (HTCN), propenesultone (PST), propanesultone (PS), lithium tetrafluoroborate ($LiBF_4$), lithium difluorophosphate ($LiPO_2F_2$), and 2-fluoro biphenyl (2-FBP).

10. The electrolyte of claim 6, wherein the non-aqueous organic solvent is composed of only chain carbonate.

11. The electrolyte of claim 10, wherein the chain carbonate is represented by Chemical Formula 2:

Chemical Formula 2

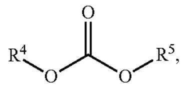

and wherein, in Chemical Formula 2

$R^4$ and $R^5$ are each independently a substituted or unsubstituted C1 to C20 alkyl group.

12. The electrolyte of claim 6, wherein the non-aqueous organic solvent is at least two selected from among dimethyl carbonate (DMC), diethyl carbonate (DEC), dipropyl carbonate (DPC), methylpropyl carbonate (MPC), ethylpropyl carbonate (EPC), and ethylmethyl carbonate (EMC).

13. A rechargeable lithium battery, comprising a positive electrode comprising a positive electrode active material;

a negative electrode comprising a negative electrode active material; and the electrolyte of claim 6.

14. The rechargeable lithium battery of claim 13, wherein the positive electrode active material comprises a cobalt-free lithium nickel manganese oxide.

15. The rechargeable lithium battery of claim 14, wherein the cobalt-free lithium nickel manganese oxide comprises lithium composite oxide represented by Chemical Formula 4:

Chemical Formula 4

$Li_aNi_xMn_yM1_zM2_wO_{2\pm b}X_c$, and wherein, in Chemical Formula 4, $0.9 \leq a < 1.2$, $0 \leq b < 0.1$, $0 \leq c < 0.1$, $0 \leq w < 0.1$, $0.6 \leq x < 1.0$, $0 < y < 0.4$, $0 < z < 0.1$, $w+x+y+z=1$, M1 and M2 are each independently at least one element selected from among Al, Mg, Ti, Zr, Cr, Sr, V, B, W, Mo, Nb, Si, Ba, Ca, Ce, Cr, Fe, and Nb, and X is at least one element selected from among S, F, P, and Cl.

16. The rechargeable lithium battery of claim 15, wherein Chemical Formula 4 is represented by Chemical Formula 4-1:

Chemical Formula 4-1

$Li_aNi_{x1}Mn_{y1}Al_{z1}M2_{w1}O_{2\pm b}X_c$, and wherein, in Chemical Formula 4-1, $0.9 \leq a < 1.2$, $0 \leq b < 0.1$, $0 \leq c < 0.1$, $0 \leq w1 < 0.1$, $0.6 \leq x1 < 1.0$, $0 < y1 < 0.4$, $0 < z1 < 0.1$, $w1+x1+y1+z1=1$, M2 is an element selected from among Mg, Ti, Zr, Cr, Sr, V, B, W, Mo, Nb, Si, Ba, Ca, Ce, Cr, Fe, and Nb, and X is at least one element selected from among S, F, P, and Cl.

17. The rechargeable lithium battery of claim 16, wherein in Chemical Formula 4-1, x1 is $0.6 \leq x1 \leq 0.79$, y1 is $0.2 \leq y1 < 0.39$, and z1 is $0.01 \leq z1 < 0.1$.

18. The rechargeable lithium battery of claim 13, wherein the negative electrode active material comprises at least one selected from among graphite and Si composite.

19. The rechargeable lithium battery of claim 18, wherein the Si composite comprises a core comprising Si-based particles and an amorphous carbon coating layer.

20. The rechargeable lithium battery of claim 19, wherein the Si-based particles comprise at least one selected from among Si particles, a Si—C composite, $SiO_x$ ($0 < x \leq 2$), and a Si alloy.

21. The rechargeable lithium battery of claim 13, wherein the rechargeable lithium battery has a charging upper limit voltage of greater than or equal to about 4.45 V.

* * * * *